(12) United States Patent
Huppert

(10) Patent No.: US 7,465,284 B2
(45) Date of Patent: Dec. 16, 2008

(54) ANKLE SUPPORT

(76) Inventor: Aaron Huppert, 215 W. 95th St., Apt. 9G, New York, NY (US) 10025

( * ) Notice: Subject to any disclaimer, the term of this patent is extended or adjusted under 35 U.S.C. 154(b) by 63 days.

(21) Appl. No.: 10/364,233

(22) Filed: Feb. 11, 2003

(65) Prior Publication Data

US 2004/0158187 A1    Aug. 12, 2004

(51) Int. Cl.
*A61F 13/00* (2006.01)
*A61F 13/06* (2006.01)
*A61F 5/37* (2006.01)

(52) U.S. Cl. .............. 602/65; 602/27; 602/66; 602/75; 602/60; 128/882

(58) Field of Classification Search .......... 602/27, 602/29, 5–10, 75–19, 62, 12, 20, 21, 23, 602/41, 60, 61, 64–66, 900, 904; 128/846, 128/869, 882; 2/455, 22, 309, 311, 911
See application file for complete search history.

(56) References Cited

U.S. PATENT DOCUMENTS

| | | | | |
|---|---|---|---|---|
| 1,428,495 A * | 9/1922 | Radcliffe | ............. | 606/216 |
| 2,484,130 A * | 10/1949 | Thibault | ............. | 602/62 |
| 3,050,053 A * | 8/1962 | Peckham | ............. | 602/5 |
| 3,312,219 A * | 4/1967 | Peckham | ............. | 602/65 |
| 3,584,622 A * | 6/1971 | Domenico | ............. | 602/65 |
| 3,695,258 A * | 10/1972 | Castle | ............. | 602/6 |
| 3,971,374 A * | 7/1976 | Wagner | ............. | 602/58 |
| 3,989,041 A * | 11/1976 | Davies | ............. | 602/62 |
| 4,094,316 A * | 6/1978 | Nathanson | ............. | 602/42 |
| 4,141,358 A | 2/1979 | DeMarco | ............. | 128/166 |
| 4,245,630 A * | 1/1981 | Lloyd et al. | ............. | 604/358 |
| 4,345,590 A * | 8/1982 | Nakajima | ............. | 602/65 |
| 4,875,476 A * | 10/1989 | Garcia | ............. | 602/65 |
| 4,905,715 A * | 3/1990 | Johnson | ............. | 128/882 |
| 5,107,826 A * | 4/1992 | Andersson | ............. | 602/19 |
| 5,154,690 A * | 10/1992 | Shiono | ............. | 602/5 |
| 5,338,290 A * | 8/1994 | Aboud | ............. | 602/75 |
| 5,514,080 A * | 5/1996 | Blott et al. | ............. | 602/5 |
| 5,613,941 A * | 3/1997 | Prengler | ............. | 602/13 |
| 5,653,224 A * | 8/1997 | Johnson | ............. | 128/200.24 |
| 5,683,354 A * | 11/1997 | Levy | ............. | 602/54 |
| 5,817,039 A * | 10/1998 | Raunig | ............. | 602/5 |
| 5,840,072 A * | 11/1998 | Carey | ............. | 604/290 |
| 5,938,631 A * | 8/1999 | Colman | ............. | 602/75 |
| 6,022,331 A * | 2/2000 | Darcey | ............. | 602/12 |
| 6,042,557 A * | 3/2000 | Ferguson et al. | ............. | 602/6 |
| 6,056,713 A | 5/2000 | Hayashi | ............. | 602/27 |
| 6,676,619 B2 * | 1/2004 | Arden | ............. | 602/8 |
| 6,719,710 B2 * | 4/2004 | Darcey | ............. | 602/8 |
| 7,195,605 B1 * | 3/2007 | White | ............. | 602/21 |
| 2003/0082973 A1 * | 5/2003 | Yamamoto et al. | ............. | 442/149 |

OTHER PUBLICATIONS 0 255 375.*
0255375.*
Konishi, 0 255 375 A1, May 1988.*

* cited by examiner

*Primary Examiner*—Patricia Bianco

(57) ABSTRACT

An ankle support having a first layer made from a rayon tape material and a second layer made from a non-woven polyester gauze material, the rayon tape material having a Young's modulus from about 2.2 N/cm$^2$ to about 3.0 N/cm$^2$ and the non-woven polyester gauze material having a bottom surface provided with an adhesive for securing the ankle support to the skin.

14 Claims, 4 Drawing Sheets

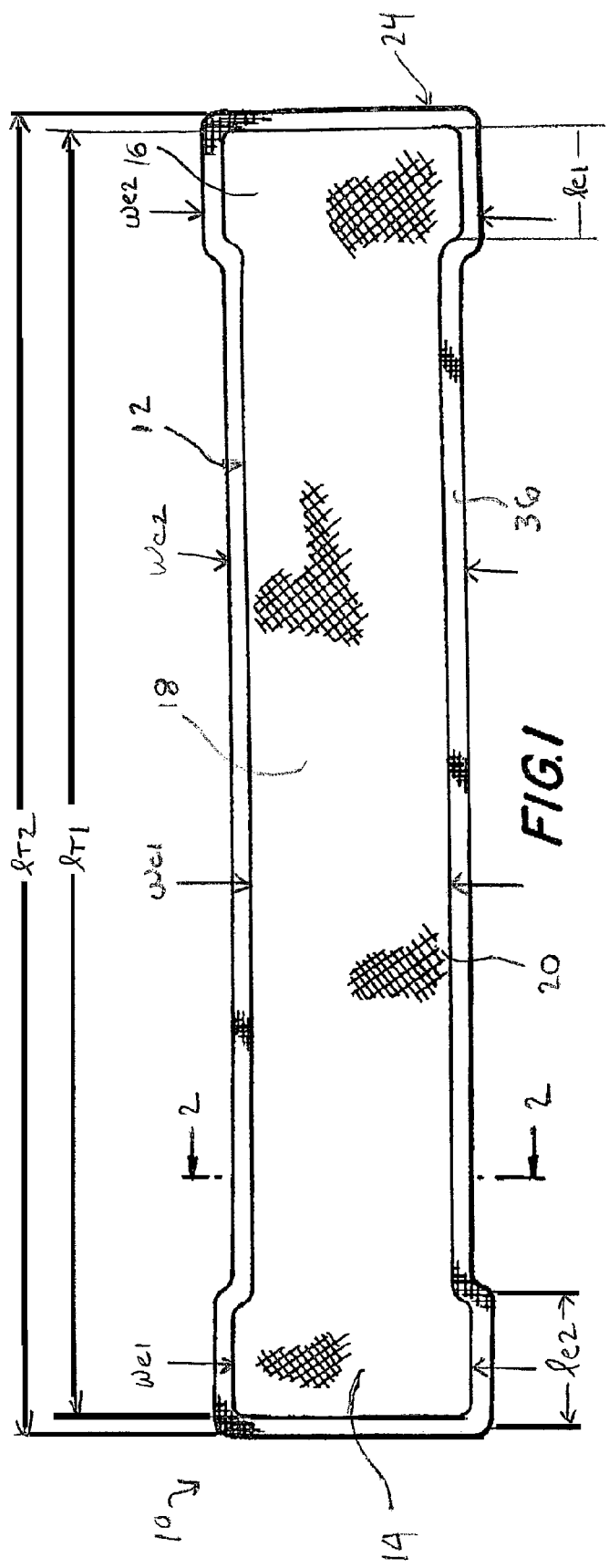
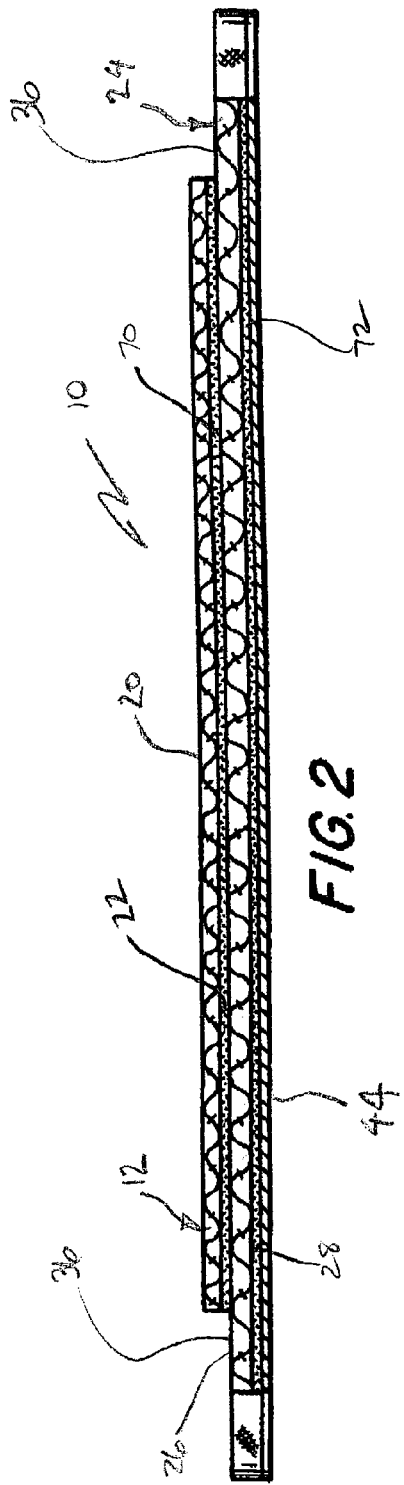

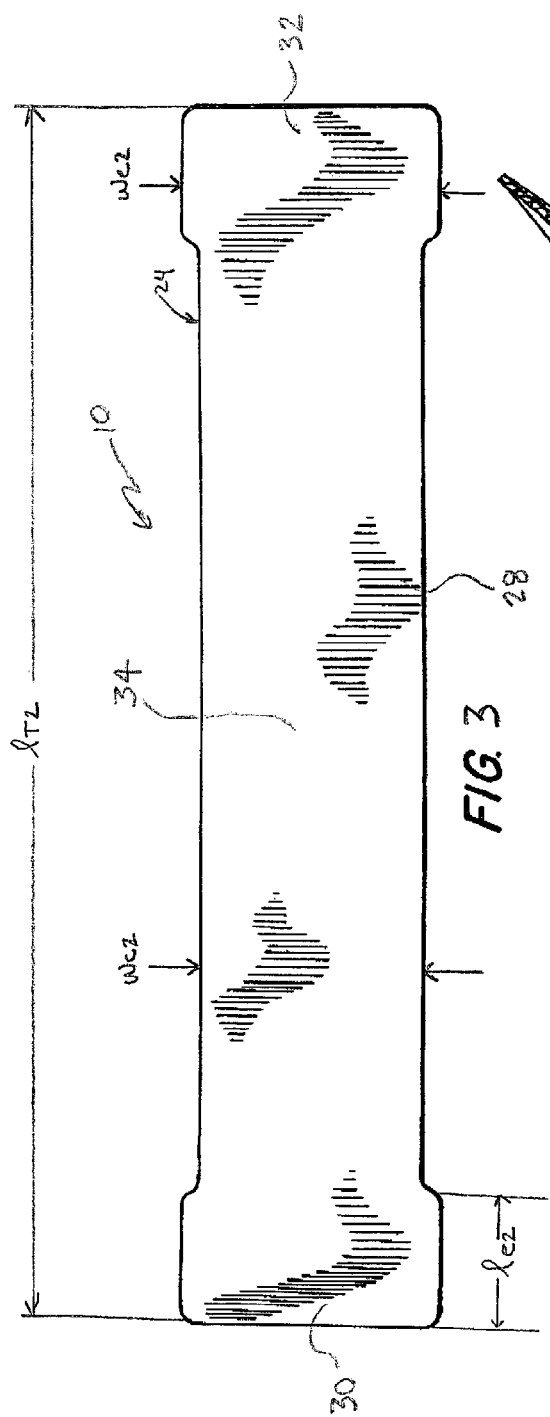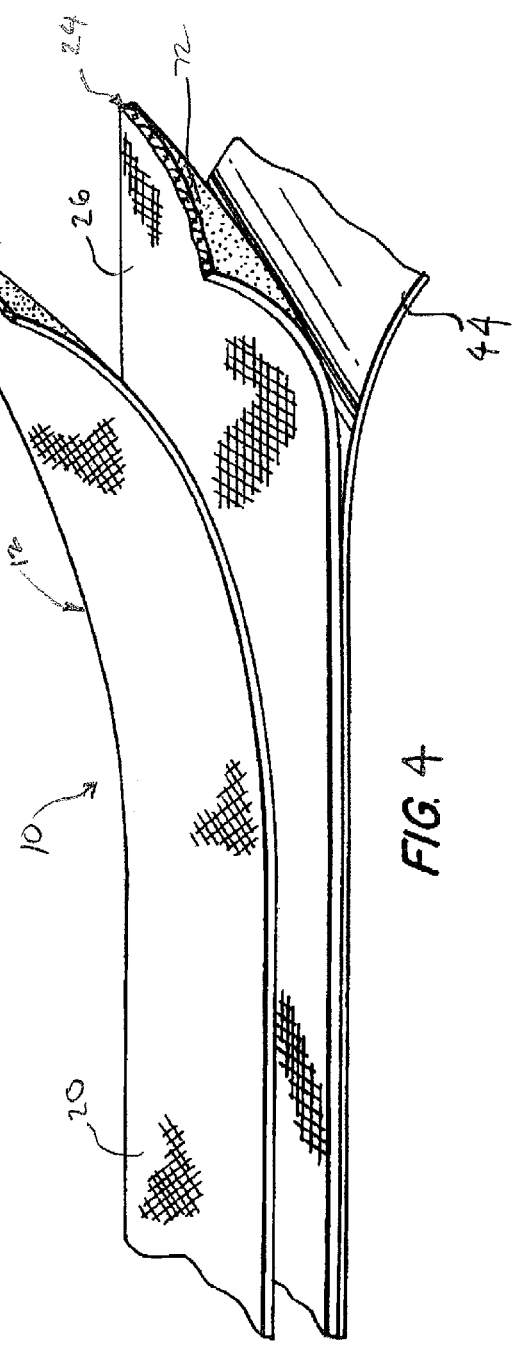

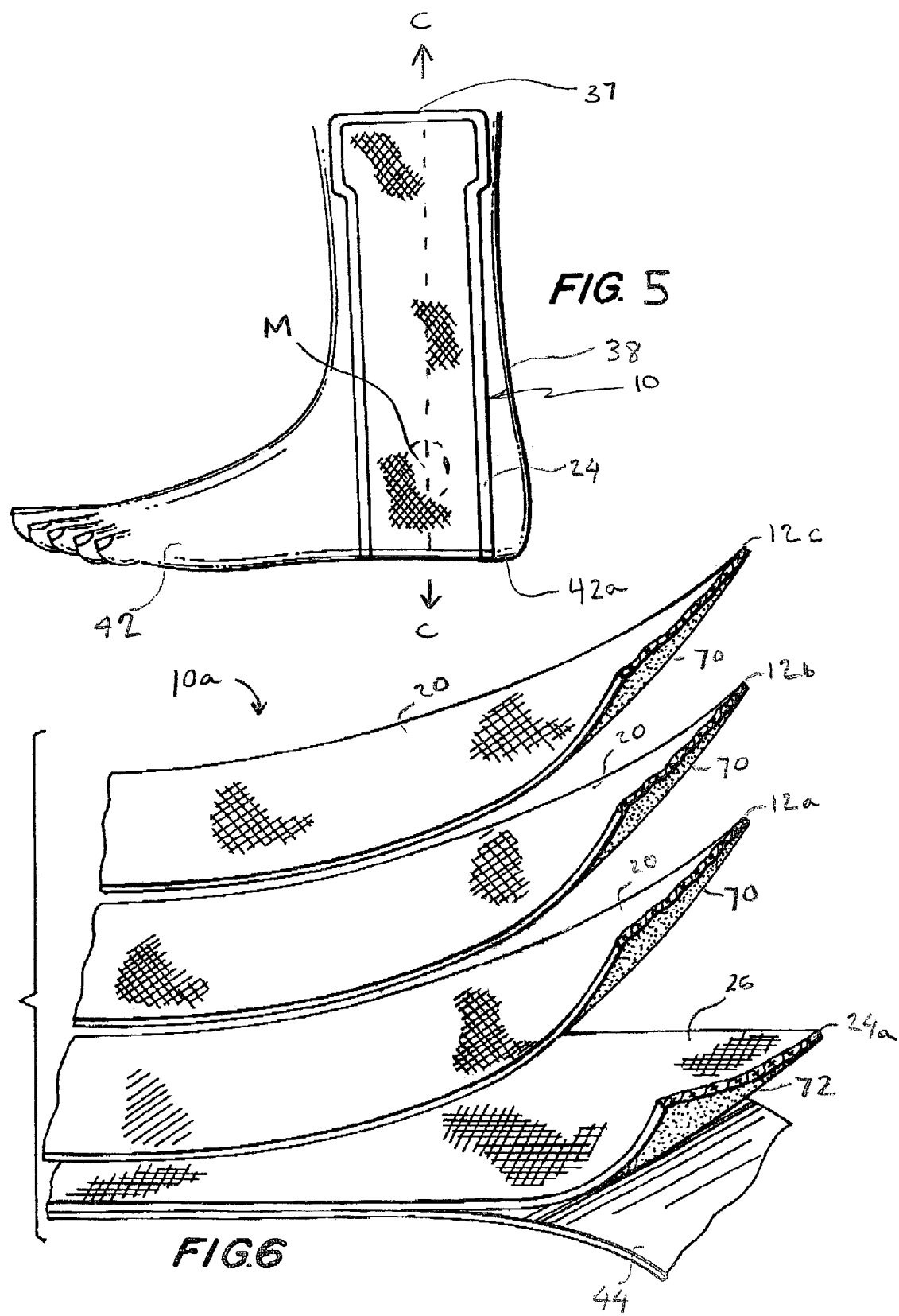

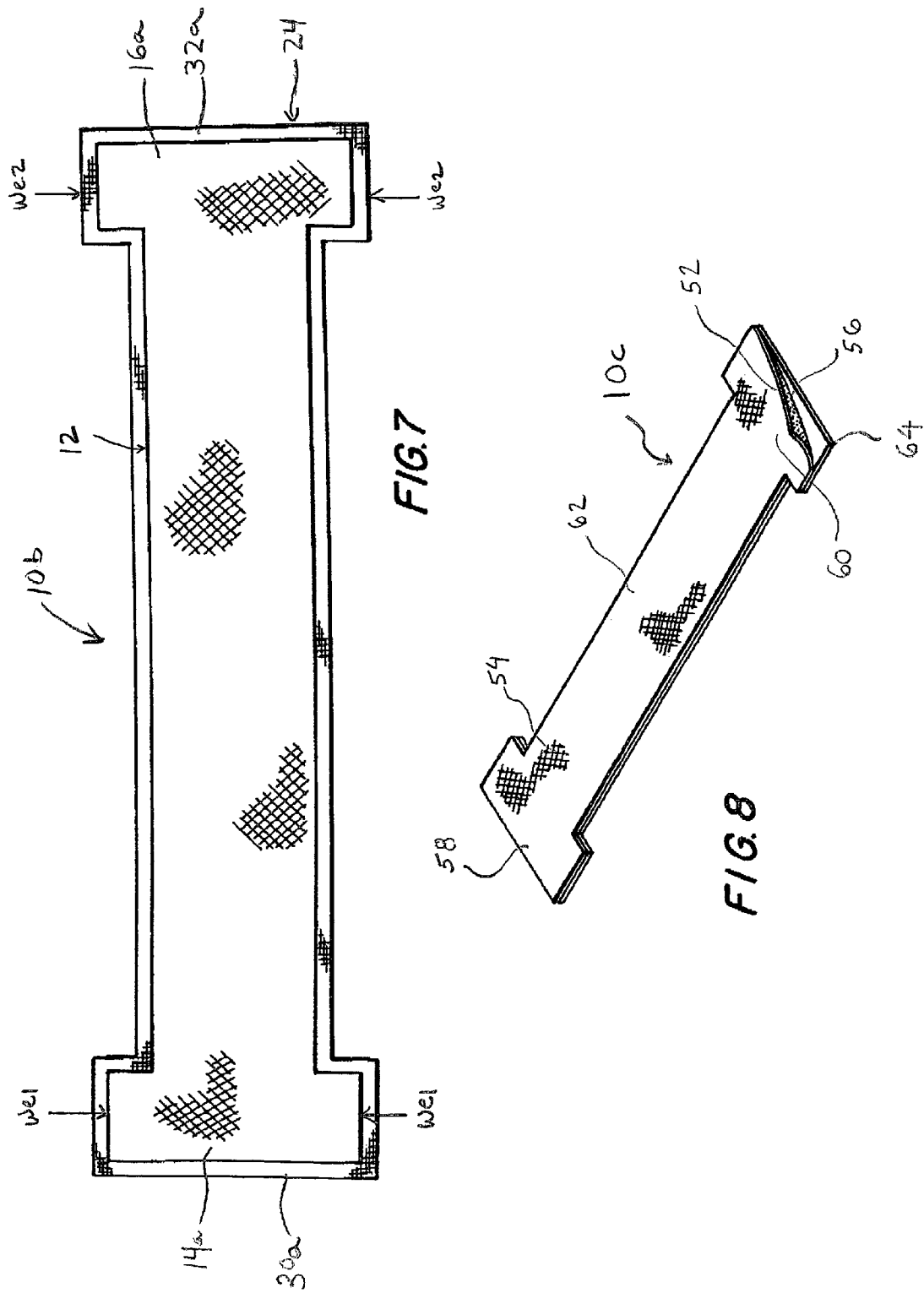

ANKLE SUPPORT

FIELD OF THE INVENTION

The present invention generally relates to ankle supports and, in particular, to a multi-layered ankle support having a first layer providing structural stiffness to the ankle support and a second layer having an adhesive backing for adherence to the skin.

BACKGROUND OF THE INVENTION

Ankle injuries to athletes and others that participate in physical activities are common and can be debilitating. The most common injuries to the ankle are to the ligaments. A ligament is made up of multiple strands of tissue, similar to a nylon rope. A sprain results in tearing of ligaments, the tear may be a complete tear of all the ligaments or a partial tear in which only a portion of the strands that make up the ligament are torn. The lateral ligaments of the ankle are by far the most commonly injured. It is estimated that lateral ligament sprains make up approximately 85% of all ankle sprains. Typically, the lateral ligaments are injured during an "inversion" injury to the ankle. An inversion injury occurs when the foot is rolled inwardly in an excessive manner thereby causing damage to the lateral ligaments. In addition to the discomfort and impairment in mobility caused by an ankle sprain, another problem caused by ankle sprains is the increased risk of re-injury. Once an ankle has been sprained, the stretching and tearing of the ligaments leads to instability in the ankle that commonly results in re-injury. It is estimated that spraining an ankle may increase the risk of re-injury by as much as 40-75%.

In view of the above, a wide variety of ankle supports and braces are currently available in a multitude of shapes, designs and materials which attempt to prevent ankle sprains and re-injury by providing additional lateral support to the ankle. Generally, prior art ankle supports fall within one of two broad categories which are discussed in further detail below.

One group of prior art ankle supports are "wrap" type supports. Such "wrap" type supports typically comprise a substantially flexible material that is tightly wrapped around the ankle to provide additional lateral support.

Normally, "wrap" type supports are applied in one of two ways. The first way is by applying a preparatory tape (i.e. "pre-wrap") or partial sock to the ankle and then wrapping layers of athletic tape on top of the preparatory tape layer such that a plurality of overlapping layers are applied to the ankle. A shortcoming of this technique is that the application of such a support requires several layers of tape that must be applied by another person, such as a trained technician or doctor. Moreover, the application of the support can be time consuming. Another disadvantage of this technique is that if the plurality of tape layers are applied improperly, the taping may cause interference with proper blood circulation. Still another disadvantage with conventional ankle wrapping techniques is that the layers of tape cannot be applied in a uniform manner which results in irregularities in the degree of support, and the direction of support, provided at different locations in the support.

An example of a "wrap" type support is illustrated in U.S. Pat. No. 5,938,631 to Colman (hereinafter "the '631 patent"). The '631 patent purports to disclose a method for taping an ankle or joint. As shown in FIGS. 4 and 5 of the '631 patent, the ankle 26 and the forefoot area 24 is first wrapped with preparatory tape 22. A stirrup 28, made from a metal backed tape T is the applied over the sole 30. Thereafter, as shown in FIG. 5, the stirrup 28 is wrapped over with conventional adhesive tape.

The second type of ankle support found in the prior art are those braces that employ one or more rigid members that are secured to the ankle by a flexible strap, tape or the like. These "rigid" braces contain at least one rigid part constructed from a thermoplastic material, metal or some other rigid material. The rigid piece or pieces of the brace are normally arranged near the medial and lateral malleoli and serve to minimize the inversion and eversion movement of the ankle. A common shortcoming with "rigid" type braces is that they often experience slippage during use. Accordingly, the brace may cause chaffing of the skin and discomfort after extended use. Another disadvantage of "rigid" type braces is that they are often rather bulky and heavy. Still another disadvantage of a brace of this type is that they restrict the user's accessory range of motion, e.g. dorsiflexion and plantarflexion, thereby limiting optimal athletic performance. Yet another disadvantage of braces of this type it that they do not adhere to the skin. Therefore, they do not provide the necessary proprioceptive feedback to the user to limit the likelihood of injury to the ankle.

An example of a "rigid" type brace is illustrated in U.S. Pat. No. 6,056,713 to Hayashi (hereinafter "the '713 patent"). The '713 patent purports to disclose an ankle brace 10 having a thermoplastic sheet 11 which is heated and molded to the ankle of the user. A cushioning material 24 made of a resilient foam material is provided on an inner surface of the ankle brace 10. As seen in FIGS. 1 and 5 of the '713 patent, the ankle brace 10 is held in place around the ankle by a strap 28 of loop textured material (i.e. VECLRO) having a buckle 29 that wraps around an upper portion 20 of the thermoplastic sheet 11 and is fastened in place with a hook textured material pad 40. Ankle strap 32 holds the medial and lateral extensions 12 and 14 of the lower portion of the thermoplastic sheet 11 around the ankle.

OBJECTS AND SUMMARY OF THE INVENTION

It is therefore an object of the present invention to avoid the above drawbacks of prior art ankle supports and braces.

It is another object of the present invention to provide a new and improved ankle support which directly adheres to the skin without slippage and effectively provides support of the ankle and without interference with the blood circulation.

It is a further object of the present invention to provide an ankle support that is easily applied and removed by the user without the aid of another trained party.

It is still another object of the present invention to provide a new and improved ankle support that is lightweight and does not cause skin irritation by adhering too tightly to the skin and yet does not move once it is applied to the skin.

Yet another object of the present invention is to provide an ankle support that allows accessory ranges of motion without tearing or ripping of the support.

Still another object of the present invention is to provide an ankle support that provides prorioceptive feedback that allows the peroneal muscles to react more rapidly to inhibit extreme ankle inversion.

In accordance with the above objectives, an ankle support according to a first aspect of the invention is provided which includes at least a first layer having a top surface and a bottom surface and at least a second layer having a top surface and a bottom surface. The second layer is coupled to the first layer such that the bottom surface of the first layer abuts the top surface of the second layer. The bottom surface of the second layer is provided with adhesive for securing the ankle brace to the skin. The first layer is constructed from a material having a Young's modulus from about 2.2 N/cm$^2$ to about 3.0 N/cm$^2$.

According to another aspect of the invention, an ankle support is provided which includes at least one layer having a top surface and a bottom surface, the bottom surface having an adhesive for securing the ankle support to the skin, wherein the at least one layer is constructed from a material having a Young's modulus from about 2.2 N/cm$^2$ to about 3.0 N/cm$^2$.

According to yet another aspect of the invention, an ankle support is provided that includes at least one layer having a top surface, a bottom surface, a center portion and first and second end portions, wherein the bottom surface is provided with an adhesive for securing the ankle support the skin, and wherein each of the end portions has a width that is greater than a width of the center portion.

According to further aspect of the invention, an ankle support is provided that includes a first layer, the first layer including a top surface, a bottom surface, a center portion, and identical end portions, each of the end portions being wider than the center portion. The ankle support further includes a second layer, the second layer including a top surface, a bottom surface having an adhesive, a center portion, and identical end portions, each of the end portions being wider than the center portion. The bottom surface of said first layer is fixedly attached to the top surface of the second layer, and the second layer has an overall size that is greater than that of said first layer such that a border is defined between a peripheral edge of the first layer and a peripheral edge of said second layer.

BRIEF DESCRIPTION OF THE DRAWINGS

A more complete appreciation of the present invention and many of the attendant advantages thereof will be readily understood by reference to the following detailed description when taken in conjunction with the accompanying drawings, in which:

FIG. 1 is a top plan view of an ankle support in accordance with the invention;

FIG. 2 is a cross sectional view of the ankle support of FIG. 1 taken along the line 2-2 of FIG. 1;

FIG. 3 is a bottom plan view of the ankle support of FIG. 1;

FIG. 4 is a partial exploded view of the ankle support of FIG. 1;

FIG. 5 is a side elevational view showing the ankle support of FIG. 1 applied to the ankle;

FIG. 6 is a partial exploded view of an ankle support in accordance with a second embodiment of the present invention;

FIG. 7 is a top plan view of an ankle support in accordance with a third embodiment of the present invention; and FIG. 8 is a perspective view of a fourth embodiment of the present invention.

DETAILED DESCRIPTION OF THE INVENTION

Referring now to the figures in which like reference characters designate identical or corresponding parts throughout the several views, and more particularly to FIGS. 1-4, a first embodiment of the ankle support in accordance with the present invention is identified generally by the reference numeral 10. The ankle support 10 includes a first layer 12 having a top surface 20 and a bottom surface 22, enlarged end sections 14, 16 and a center section 18 extending between the end sections 14, 16. The ankle support further includes a second layer 24 having a top surface 26 and a bottom surface 28, ends sections 30, 32 and a center section 34. The bottom surface 22 of the first layer 12 is affixed to the top surface 26 of the second layer 24 using an adhesive interlayer 70. The adhesive layer 70 may be a zinc-oxide type adhesive. Preferably, the adhesive used to form adhesive layer 70 has an adhesive strength of about 3.5 N/cm to about 5.0 N/cm as measured by the adhesive power on steel test. Other suitable adhesives are also well known in the art and may be utilized to form adhesive layer 70.

Referring to FIG. 2, the bottom surface 28 of the second layer 24 is covered with an adhesive layer 72 for affixing the support 10 to the ankle in the manner shown in FIG. 5. The adhesive of layer 72 adheres firmly to the skin to prevent movement of the brace during use. The adhesive of layer 72 covering the bottom surface 28 of the second layer 24 is hypo-allergenic and non-inflammatory and is preferably acrylic. However other suitable materials could be used. Preferably, the adhesive strength of the adhesive of layer 72 is in the range of about 1.6 N/cm to about 2.6 N/cm. The adhesive strength is measured using the adhesive power on steel test.

As best seen in FIG. 4, prior to the application of the support to the ankle, the exposed surface of the adhesive layer the exposed surface of adhesive layer 72 is covered by a peel away strip 44 which is removed from the adhesive layer 72 prior to application of the support 10 to the skin.

The first layer 12 of the ankle support 10 is preferably a rayon tape that provides relative stiffness to the ankle support 10 and lateral support to the ankle when the support is applied to the ankle. Preferably, the Young's modulus of the first layer 12 is in the range of about 2.2 N/cm$^2$ to about 3.0 N/cm$^2$. Leukotape P® tape, a product of BSN Medical, may be used as the first layer, having a Young's modulus of about 2.6 N/cm$^2$. Leukotape P® tape is provided with an adhesive layer, i.e. adhesive interlayer 70, on one surface thereof. The adhesive used on Leukotape P® tape has an adhesive strength of about 3.5 N/cm to about 5.0 N/cm as measured by the adhesive power on steel test.

The second layer 24 of the ankle support 10 is preferably a non-woven polyester gauze material or the like. Cover-Roll Stretch® tape, a product of BSN Medical, may be used as the second layer. Cover-Roll Stretch® tape is provided with an adhesive layer, i.e. adhesive layer, on one surface thereof for attaching the tape to the skin. The adhesive used on Cover-Roll Stretch® has an adhesive strength of about 2.1 N/cm.

Referring to FIG. 1, the first layer 12 is shaped so it that includes enlarged end sections 14 and 16 and a center section 18 that extends between the enlarged end sections 14 and 16. Each of the end sections 14 and 16 has a width $w_{e1}$ that is wider than a width $w_{c1}$ of the center section 18. The length of each of the end sections 14 and 16 has been designated as $l_{e1}$ and the total length of the first layer 12 has been designated as $l_{T1}$.

As best seen in FIG. 3, the second layer is also shaped so that it includes enlarged end sections 30 and 32 and a center section 34. Each of the end sections 30 and 32 has a width $w_{e2}$ that is wider than a width $w_{c2}$ of the center section 34. The length of each of the end sections 14 and 16 has been designated as $l_{e1}$ and the total length of the first layer 12 has been designated as $l_{T1}$.

Typical dimensions of the first layer 12 and the second layer 24, for a person of average size, would be approximately as follows:

| DIMENSION | FIRST LAYER (12) | SECOND LAYER (24) |
|---|---|---|
| Total Length | 18.5" ($l_{T1}$) | 19.0" ($l_{T2}$) |
| Center Portion Width | 2.5" ($w_{c1}$) | 3.0" ($w_{c2}$) |
| End Portion Width | 3.0" ($w_{e1}$) | 3.5" ($w_{e2}$) |
| End Portion Length | 1.75" ($l_{e1}$) | 2.0" ($l_{e2}$) |

Using the above dimensions, the border 36 defined about the peripheral edge of the support is ¼". The dimensions provided in the above table may have a value within the following ranges: ($w_{c1}$) 1.5" to 2.5"; ($w_{c2}$) 2.0" to 3.0"; ($w_{e1}$) 2.0" to 3.0"; ($w_{e2}$) 2.5" to 3.5"; ($l_{e1}$) 1.25" to 2.25"; ($l_{e2}$) 1.5" to 2.5".

The total length (i.e. $l_{T1}$, $l_{T2}$) of the first layer 12 and second layer 24 is selected according to the height of the person using the support. Specifically, to obtain optimum performance and support, the total length of the first layer 12 and second layer 24 are selected such that during use, a terminal top edge 37 (FIG. 5) of the second layer 24 terminates about 4" to about 6" above the center of the medial lateral malleoli "M". A table is provided below which provides the preferred approximate lengths of the first layer 12 and second layer 24 relative to the height of the person using the support.

| Height of Person | Length of First Layer ($l_{T1}$) | Length of Second Layer ($l_{T2}$) |
|---|---|---|
| Up to 5'0" | 12.5" | 13" |
| 5'0" to 5'4" | 14.5" | 15" |
| 5'4" to 5'8" | 16.5" | 17" |
| 5'8" to 6'0" | 18.5" | 19" |
| 6'0" to 6'4" | 20.5" | 21" |
| 6'4" and up | 22.5" | 23" |

Referring now to FIG. 5, the ankle support 10 is applied to the ankle 38 as follows. First, the peel away release strip 44 is removed thereby exposing the adhesive layer 72 on the bottom surface 28 of the second layer 24. Then the ankle support 10 is applied to the sole of the foot under the heel area 42a as shown such that a central portion of the ankle support is arranged under the foot and equal portions of the ankle support extend upwardly along each side of the ankle. Once the support 10 is applied, the user firmly presses the support against the skin such that the adhesive layer 72 on the second layer 24 securely attaches the support 10 to the ankle. The enlarged end portions 14 and 16 of the first layer 12, and the enlarged end portions 30 and 32 of the second layer 24, partially extend around the ankle to promote secure attachment of the ankle support 10 to the ankle. However, the end portions 14, 16, 30 and 32 do not entirely wrap around the entire the circumference of the ankle. It has been found that this configuration improves the durability of the support by decreasing the likelihood of the support 10 tearing while at the same time permits the accessory ranges of motion necessary for optimum athletic performance.

The ankle support is arranged on the foot and ankle such that a centerline "C" of the ankle support 10 passes substantially over center of the medial and lateral malleoli "M" on each side of the ankle. Further, the ankle support is arranged on the foot and ankle such that each terminal edge 37 of the second layer 24 terminates about 4" to about 6" above the center of the medial and lateral malleoli. As shown, when applied to the ankle the width $w_{c1}$ of the center portion 18 of the first layer 12 and the width $w_{c2}$ of the center portion 34 of the second layer are sufficiently wide so as to cover the medial and lateral malleoli "M".

The embodiment of the present invention described above overcomes the shortcomings and problems inherent in prior art supports and braces and provides additional advantages and benefits. Specifically, the present invention provides an ankle support that provides sufficient lateral support to prevent injury and re-injury resulting from inversion of the ankle, while at the same time permits accessory ranges of motion necessary for optimal athletic performance. This benefit is achieved primarily by the first layer 12 material, which has a Young's modulus from about 2.2 N/cm$^2$ to about 3.0 N/cm$^2$. It is has been found that a material with a Young's modulus in this range provides sufficient lateral support to prevent injury while at the same time permitting the requisite accessory ranges of motion. Further, due to the simplified structure of the ankle support 10 relative to prior art supports the support of the present invention may be easily applied and removed by the user, thereby eliminating the need for a trained physician or technician. The ankle support 10 of the present invention also overcomes the slippage problem found by users when wearing prior art braces and supports. The ankle support 10 of the present invention avoids the slippage problems found in the prior art braces and supports since the ankle support 10 is applied directly to the skin by adhesive layer 72 on the bottom surface 28 of the second layer 24. The large skin to adhesive contact area significantly reduces slippage and improves comfort of the brace during use. In addition, the enlarged end portions 14, 16 of the first layer 12 and the enlarged end portions 30, 32 of second layer 24 promote the secure attachment of the ankle support 10 to the ankle while at the same time permit the accessory ranges of motion necessary for optimum athletic performance. Further, the close support to skin contact improves proprioceptive feedback to the user necessary to limit the likelihood of injury to the ankle.

Reference is now made to FIG. 6 which depicts a second embodiment of the ankle support 10a according to the present invention. Where applicable the same reference numbers have been used to designate identical or corresponding elements as those described with reference to the embodiment shown in FIGS. 1-5.

The ankle support 10a includes a plurality of identically constructed support layers 12a, 12b and 12c. Each of these layers, 12a, 12b and 12c, is provided with an adhesive 70 on the bottom surface 22 thereof in the same manner as described above. As shown, layer 12c is secured to layer 12b by placing the bottom surface 22 thereof in face to face abutment with the top surface 20 of layer 12b. Likewise, layer 12b is secured to layer 12a by placing the bottom surface 22 thereof in face to face abutment with the top surface 20 of layer 12a. Further, layer 12a is secured to layer 24 by placing the bottom surface 22 thereof in face to face abutment with the top surface 26 of base layer 24a.

Each of the layers 12a, 12b and 12c may be constructed from Leukotape P® tape as discussed above with regard to the first embodiment. Base layer 24a may be constructed from Cover-Roll Stretch® tape as discussed above with regard to the first embodiment.

The bottom surface 28 of the base layer 24a is provided with an adhesive 72 in the same manner as discussed above with regard to the first embodiment. Thus, the ankle support 10a is secured to the ankle in the same manner as the ankle support 10 of the first embodiment.

The physical dimensions (i.e., total length, center portion width, etc.) and overall shape of the layers 12a, 12b and 12c are the same as those set forth above for layer 12 with regard to the first embodiment. Likewise, the physical dimensions (i.e. total length, center portion width, etc.) and shape of layer 24a are the same as those set forth above for layer 24 with regard to the first embodiment.

Although FIG. 6 depicts the ankle support 10a as having three support layers 12a, 12b and 12c it is appreciated that any reasonable number of support layers could be employed depending upon the degree of support desired.

Reference is now made to FIG. 7 which depicts a third embodiment of the ankle support 10b according to the present invention. Where applicable the same reference numbers have been used to designate identical or corresponding elements with reference to the embodiment shown in FIGS. 1-5. The embodiment shown in FIG. 7 is identical in all respects to the embodiment shown in FIGS. 1-5 except that in the embodiment shown in FIG. 7 the ankle support is provided with T-shaped end portions rather than the bone-shaped end portions of the first embodiment. That is, the first layer 12 is provided with T-shaped end portions 14a and 16a and the second layer 24 is provided with T-shaped end portions 30a and 32a. The width $w_{e2}$ of the end portions 30a and 32a of the second layer 24 are preferably from about 3.5" to about 5.5". The width $w_{e2}$ of the end portions 14a and 16a of the first layer are preferably from about 3.0" to about 5.0". All of the other dimensions of the ankle support 10b are the same as those discussed above with regard to the first embodiment.

Reference is now made to FIG. 8 which depicts a fourth embodiment 10c of the ankle support according to the present invention. The ankle support 10c shown in FIG. 8 comprises only a single layer 52 having a top surface 54, a bottom surface 56, end portions 58 and 60 and a center portion 62. Layer 52 is preferably constructed from a rayon tape having a Young's modulus in the range of 2.2 N/cm² to 3.0 N/cm². The bottom surface 56 is provided with an adhesive that is hypo-allergenic and non-inflammatory and is preferably acrylic. However other suitable adhesives could be used. Preferably, the adhesive strength of the adhesive used on the bottom surface 56 is in the range of 1.6 N/cm to 2.6 N/cm. The adhesive strength is measured using the adhesive power on steel test. Acrylic adhesives having the properties described above are well known to those in the art and do not require any further description herein. The embodiment shown in FIG. 8 may include either the bone-shaped end portions of the type included in the first embodiment (FIGS. 1-5) or the T-shaped end portions of the type included in the third embodiment (FIG. 7). If the embodiment shown in FIG. 8 is provided with bone-shaped end portions its dimensions (i.e. total length, center portion width, etc.) would be the same as those set forth above in connection the first embodiment. If the embodiment shown in FIG. 8 is provided with T-shaped end portions its dimensions (i.e. total length, center portion width, etc.) would be the same as those set forth above in connection with the third embodiment.

Although exemplary embodiments of the present invention has been shown and described, it will be apparent to those having ordinary skill in the art that a number of changes, modifications or alterations may be made, none of which depart from the spirit of the present invention. All such changes, modifications or alterations should therefore be seen as within the scope of the present invention.

I claim:

1. A support for a patient's ankle consisting of:
a generally "bone-shaped" support configured to include at least a first layer and a second layer, said support having an overall length terminating in enlarged, "bone-shaped" end sections, wherein the entire support is lightweight;
said at least first layer having an overall length, a top surface, a bottom surface, a peripheral edge, enlarged end portions each having a $width_e$ and a $lenght_e$, and a center portion having a $width_c$ and extending between said enlarged end portions, wherein said end portions $width_e$ is wider than said center $width_c$, and wherein the bottom surface of said at least first layer has an adhesive thereon and said adhesive has an adhesive strength of from about 3.0 N/cm to about 5.0 N/cm, and wherein said at least first layer comprises a material having a Young's modulus of from about 2.2 N/cm2 to about 3.0 N/cm2 to provide structural support to said ankle;
said second layer having an overall length that is greater than the first layer, a top surface, a bottom surface, a peripheral edge, enlarged end portions each having a $width_{e2}$ and a $lenght_{e2}$, and a center portion extending between the end sections having a $width_{c2}$ and extending between said enlarged end portions, wherein said end portions $width_{e2}$ is wider than said center $width_{c2}$;
said second layer being affixed to said first layer using an adhesive interlayer, such that the entire bottom surface of said first layer abuts said top surface of said second layer such that a border is defined around the perimeter of said first layer between each of said peripheral edges of said first layer and each of said corresponding peripheral edges of said second layer;
the bottom surface of said second layer further having an adhesive for securing said second layer to the patient's ankle, the adhesive being hypo-allergenic and non-inflammatory; and
wherein said "bone-shaped" support is configured such that, during use, the total length of said first layer and said second layer is selected according to the height of the patient to provide optimal lateral support such that a terminal top edge of the second layer terminates at a desired location above the center of a medial and lateral malleoli of the ankle, thereby decreasing the likelihood of tearing and thereby facilitating accessory ranges of motion.

2. The ankle support of claim 1, wherein the support is adapted to be positioned from one lateral surface of a patient's ankle down to and underneath a space between a patient's heel and instep and then upward to the opposite lateral surface of the patient's ankle.

3. The ankle support of claim 1, wherein said center portion of said first layer has a $width_c$ from about 1.5" to about 2.5" and each of said end portions of said first layer has a $width_e$ from about 2.0" to about 3.0", and wherein said center portion of said second layer has a $width_{c2}$ from about 2.0" to about 3.0" and each of said end portions of said second layer has a $width_{e2}$ from about 2.5" to about 3.5".

4. The ankle support of claim 3, wherein said center portion of said first layer has a $width_c$ of about 2.5" and each of said end portions of said first layer has a $width_e$ of about 3.0", and wherein said center portion of said second layer has a $width_{c2}$ of about 3.0" and each of said end portions of said second layer has a $width_{e2}$ of about 3.5".

5. The ankle support of claim 1, wherein said first layer has a total length of about 12.5" to about 22.5" and said second layer has a total length of about 13.0" to about 23.0".

6. The ankle support of claim 5, wherein said first layer has a total length of about 18.5" and said second layer has a total length of about 19.0".

7. The ankle support of claim 1, wherein each of said end portions of said first layer has a $length_e$ of from about 1.25" to about 2.25" and each of said end portions of said second layer has a $length_{e2}$ of from about 1.5" to about 2.5".

8. The ankle support of claim 7, wherein each of said end portions of said first layer has a $length_e$ of about 1.75" and each of said end portions of said second layer has a $length_{e2}$ of about 2.0".

9. The ankle support of claim 1, wherein said first layer is rayon.

10. The ankle support of claim 1, wherein said second layer is a non-woven polyester gauze material.

11. The ankle support of claim 1, wherein said adhesive on said first layer is an acrylic based adhesive.

12. The ankle support of claim 1, wherein said adhesive on said first layer is a zinc-oxide adhesive.

13. The ankle support of claim 1, wherein said adhesive on said first layer has an adhesive strength in the range from about 3.5 N/cm to about 5.0 N/cm.

14. The ankle support of claim 1, wherein a removable flexible polymer sheet is positioned on the adhesive layer on the bottom surface of the second layer.

* * * * *